United States Patent
Nishiura

(10) Patent No.: US 12,180,322 B2
(45) Date of Patent: Dec. 31, 2024

(54) PROTEIN ADSORPTION PREVENTING AGENT, PROTEIN ADSORPTION PREVENTING FILM, AND MEDICAL TOOL USING SAME

(71) Applicant: Maruzen Petrochemical Co., Ltd., Chuo-ku (JP)

(72) Inventor: Takao Nishiura, Ichihara (JP)

(73) Assignee: Maruzen Petrochemical Co., Ltd., Chuo-ku (JP)

( * ) Notice: Subject to any disclaimer, the term of this patent is extended or adjusted under 35 U.S.C. 154(b) by 821 days.

(21) Appl. No.: 16/623,185

(22) PCT Filed: Apr. 6, 2018

(86) PCT No.: PCT/JP2018/014738
§ 371 (c)(1),
(2) Date: Dec. 16, 2019

(87) PCT Pub. No.: WO2019/003558
PCT Pub. Date: Jan. 3, 2019

(65) Prior Publication Data
US 2021/0122867 A1    Apr. 29, 2021

(30) Foreign Application Priority Data
Jun. 26, 2017 (JP) .................. 2017-124013

(51) Int. Cl.
| | | |
|---|---|---|
| *C08F 297/00* | (2006.01) | |
| *A61L 31/10* | (2006.01) | |
| *A61L 31/14* | (2006.01) | |
| *C08F 216/14* | (2006.01) | |
| *C09D 129/10* | (2006.01) | |
| *C09D 153/00* | (2006.01) | |

(52) U.S. Cl.
CPC ............ *C08F 297/00* (2013.01); *A61L 31/10* (2013.01); *A61L 31/14* (2013.01); *C08F 216/1433* (2020.02); *C09D 129/10* (2013.01); *C09D 153/00* (2013.01); *A61L 2400/18* (2013.01); *A61L 2420/02* (2013.01); *A61L 2420/06* (2013.01)

(58) Field of Classification Search
None
See application file for complete search history.

(56) References Cited

U.S. PATENT DOCUMENTS

| | | |
|---|---|---|
| 4,028,295 A | 6/1977 | Loshaek |
| 2016/0250391 A1 | 9/2016 | Hirata |
| 2019/0091380 A1 | 3/2019 | Tanaka et al. |

FOREIGN PATENT DOCUMENTS

| | | | |
|---|---|---|---|
| JP | 2004-18639 A | | 1/2004 |
| JP | 2006306794 A | * | 11/2006 |
| JP | 4528601 B2 | | 8/2010 |
| JP | 2013-57058 A | | 3/2013 |
| JP | 2015-117291 A | | 6/2015 |
| JP | 2016-50266 A | | 4/2016 |
| JP | 2016-182690 A | | 10/2016 |
| JP | 2016-198426 A | | 12/2016 |
| JP | 2014/047347 | * | 3/2017 |
| WO | WO 2013/099427 A1 | | 7/2013 |
| WO | WO 2015/050036 A1 | | 4/2015 |
| WO | WO 2017/150000 A1 | | 9/2017 |
| WO | WO 2017/204306 A1 | | 11/2017 |

OTHER PUBLICATIONS

English translation of JP2016050266A (2022).*
English translation of JP2006306794A (2023).*
English translation of claims of JP2006306794A (2023).*
English translation of JP2014/047347 (2023).*
Matsuda et al. (Journal of Polymer Science: Part B: Polymer Physics 1179-1187 (2006).*
Gombotz et al. (Journal of Biomedical Materials Research, vol. 25, 1547-1562 (1947).*
Extended European Search Report issued on Nov. 23, 2020 in European Patent Application No. 18824772.0, 7 pages.
International Search Report issued on Jun. 12, 2018 in PCT/JP2018/014738 filed on Apr. 6, 2018, 2 pages.
Okano et al., "Biomaterial—fundamentals and development into advanced researches—", First impression of the first edition, Supervisor Mitsuo Okano, Publisher Minako Ozawa, Published by Tokyo Kagaku Dojin Co., Ltd., 2016, with English Translation, 28 pages.
Asanuma et al., "Biomaterial Chemistry—Fundamentals and Applications—", First impression of the first edition, Published by Corona Publishing Co., Ltd., 2015, with English Translation, 26 pages.

* cited by examiner

*Primary Examiner* — Patricia Duffy
*Assistant Examiner* — Garen Gotfredson
(74) *Attorney, Agent, or Firm* — Oblon, McClelland, Maier & Neustadt, L.L.P.

(57) ABSTRACT

To provide a protein adsorption preventing agent having an excellent film forming property and excellent water solubility, capable of easily coating various substrates, and having an excellent protein adsorption preventing property, and also to provide a protein adsorption preventing film using the protein adsorption preventing agent and a medical tool including the protein adsorption preventing film. A protein adsorption preventing agent containing an aqueous solvent and a polymer having at least a structural unit (A) represented by the following formula (1) (wherein $R^1$ represents a methyl group or an ethyl group and n represents an integer of 1 to 10), and further containing a hydrophobic group, a protein adsorption preventing film using the protein adsorption preventing agent, and a medical tool including the protein adsorption preventing film.

(1)

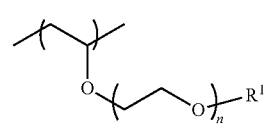

7 Claims, No Drawings

PROTEIN ADSORPTION PREVENTING AGENT, PROTEIN ADSORPTION PREVENTING FILM, AND MEDICAL TOOL USING SAME

TECHNICAL FIELD

The present invention relates to a protein adsorption preventing agent, a protein adsorption preventing film, and a medical tool using the same.

BACKGROUND ART

In recent years, a biocompatible material capable of suppressing a foreign body reaction without causing harm to a living body has attracted attention. A biocompatible material is a very broad concept, and is roughly divided into two depending on the purpose. One is an antithrombotic material aiming at prevention of blood coagulation, and the other is a protein adsorption preventing material aiming at prevention of protein adhesion. Among them, the protein adsorption preventing material is used in a wide range of fields of medical devices, sanitary products such as contact lenses, diagnostic agents, cell incubators, and the like.

As a known protein adsorption preventing material, for example, a block copolymer composed of a polymer of a (meth)acrylic acid ester monomer and a polymer of a (meth)acrylamide monomer is exemplified (PTL 1). It is known that the block copolymer has an excellent coating film forming ability and also an excellent adhesive property to a substrate, and has a property of not adsorbing a protein. However, the (meth)acrylamide monomer is known to have toxicity and the residual monomer in the copolymer may be eluted during use, and therefore, its use was limited.

Therefore, as a material having a coating film forming ability using a highly safe raw material, a vinyl ether copolymer has been developed (PTL 2). In the literature, a method for copolymerizing 2-methoxyethyl vinyl ether (MOVE) and a vinyl ether having an alicyclic skeleton such as tricyclodecane vinyl ether (TCDVE) is proposed. However, although the copolymer exhibits thermal responsiveness and can be used in a material such as an electrical, electronic, or optical material such as a display or a light shield, biocompatibility such that protein adhesion is prevented was not evaluated at all.

Further, in PTL 3, it is disclosed that a copolymer of a vinyl ether having an oxyethylene chain and a hydrophobic vinyl ether has an excellent film forming property and excellent water resistance, and also has an excellent antithrombotic property. However, the obtained copolymer is insoluble in water, and therefore, its use was sometimes limited. In addition, although the antithrombotic property was evaluated, non-adsorbability to proteins was not evaluated at all in the patent literature.

CITATION LIST

Patent Literature

PTL 1: JP-A-2013-57058
PTL 2: Japanese Patent No. 4528601
PTL 3: JP-A-2016-50266

SUMMARY OF INVENTION

Technical Problem

The present invention has been made in view of the above-mentioned circumstances, and has an object to provide a protein adsorption preventing agent having an excellent film forming property and excellent water solubility, capable of easily coating various substrates, and having an excellent protein adsorption preventing property, and also to provide a protein adsorption preventing film formed from the protein adsorption preventing agent and a medical tool using the protein adsorption preventing film.

Solution to Problem

The present inventors conducted various studies while paying attention to a polymer containing a structural unit derived from a vinyl ether, and as a result, they found that by introducing a hydrophobic group into a polymer derived from a specific vinyl ether, the polymer has an excellent film forming property and excellent water solubility, and also exhibits an excellent protein adsorption preventing property, and thus completed the present invention.

That is, the present invention is directed to a protein adsorption preventing agent containing an aqueous solvent and a polymer having at least a structural unit (A) represented by the following formula (1) and further containing a hydrophobic group.

[Chem. 1]

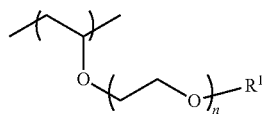

(1)

[In the formula, $R^1$ represents a methyl group or an ethyl group and n represents an integer of 1 to 10].

Further, the present invention is directed to a protein adsorption preventing film formed from the above-mentioned protein adsorption preventing agent.

Further, the present invention is directed to a medical tool including the above-mentioned protein adsorption preventing film.

Advantageous Effects of Invention

The protein adsorption preventing agent of the present invention is capable of easily coating various substrates, has an excellent film forming property and excellent water solubility, and is further capable of forming a coating film having a protein adsorption preventing property.

In addition, the protein adsorption preventing film of the present invention can prevent protein adsorption, and therefore can be favorably used for various medical tools. Further, the medical tool including a protein adsorption preventing film of the present invention can prevent fouling.

DESCRIPTION OF EMBODIMENTS

The protein adsorption preventing agent of the present invention contains a specific polymer and an aqueous solvent, and the specific polymer is a polymer containing at least a structural unit (A) represented by the following formula (1) (hereinafter simply referred to as "structural unit (A)"), and the polymer is a polymer having a hydrophobic group introduced therein (hereinafter referred to as "hydrophobic group-containing polymer").

[Chem. 2]

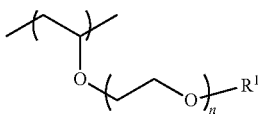
(1)

In the above formula (1), $R^1$ is a methyl group or an ethyl group, and the number n of repetitions of the oxyethylene chain is an integer of 1 to 10, preferably an integer of 1 to 6, more preferably an integer of 1 to 4, and particularly preferably an integer of 1 to 3.

The hydrophobic group contained in the hydrophobic group-containing polymer used in the protein adsorption preventing agent of the present invention is not particularly limited as long as it can lower the affinity for water, that is, impart a property of being hardly soluble in water or hardly mixed with water by being introduced into the polymer, however, for example, hydrophobic groups represented by the following formulae (2) to (4), etc. are exemplified. Among these, one type or two or more types may be contained.

Hydrophobic Group (2):

[Chem. 3]

(2)

In the above formula (2), $R^2$ is an aliphatic hydrocarbon group, specifically, a linear or branched alkyl group or alkenyl group, or a monocyclic or polycyclic alkyl group or alkenyl group.

The linear or branched alkyl group or alkenyl group has preferably 2 to 10 carbon atoms, more preferably 2 to 8 carbon atoms, further more preferably 2 to 6 carbon atoms.

Specific examples of the linear or branched alkyl group or alkenyl group include, for example, linear or branched alkyl groups such as an ethyl group, an n-propyl group, an isopropyl group, an n-butyl group, an isobutyl group, a tert-butyl group, a 1-pentyl group, a 2-pentyl group, a 3-pentyl group, a 1-(2-methyl)-butyl group, a 2-(2-methyl)-butyl group, a 1-(3-methyl)-butyl group, a 2-(3-methyl)-butyl group, a (2,2-dimethyl)-propyl group, a 1-hexyl group, a 2-hexyl group, a 3-hexyl group, a 1-heptyl group, a 2-heptyl group, a 3-heptyl group, a 4-heptyl group, a 1-octyl group, and a 1-(2-ethyl)-hexyl group; and linear or branched alkenyl groups such as a vinyl group, a 1-propenyl group, an allyl group, a 2-butenyl group, a 3-butenyl group, an isopropenyl group, an isobutenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, and a 5-hexenyl group.

Further, the monocyclic or polycyclic alkyl group or alkenyl group has preferably 3 to 25 carbon atoms, more preferably 4 to 20 carbon atoms, further more preferably 5 to 15 carbon atoms.

Specific examples of the monocyclic or polycyclic alkyl group or alkenyl group include, for example, monocyclic alkyl groups or alkenyl groups such as a cyclopentyl group, a cyclopentylmethyl group, a methylcyclopentyl group, a dimethylcyclopentyl group, a cyclohexyl group, a cyclohexylmethyl group, a methylcyclohexyl group, a dimethylcyclohexyl group, a cyclohexenyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclooctadecyl group, and a cycloicosyl group; and polycyclic alkyl groups or alkenyl groups such as a bicyclohexyl group, a decahydronaphthyl group, a norbornyl group, a methylnorbornyl group, an isoboronyl group, an adamantyl group, a tricyclodecanyl group, a tricyclodecenyl group, and a tetracyclododecyl group.

Among these aliphatic hydrocarbon groups, an n-butyl group and a cyclohexyl group are preferred from the viewpoint of a film forming property, water solubility, and a protein adsorption preventing property.

Hydrophobic Group (3):

[Chem. 4]

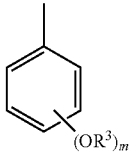
(3)

In the above formula (3), $R^3$ represents a hydrogen atom, an alkyl group having 1 to 4 carbon atoms, an alkoxyalkyl group having 2 to 6 carbon atoms, an alkanoyl group, an alkoxycarbonyl group, an alkoxycarbonylalkyl group, or an alkylsilyl group, and m is an integer of 0 to 3.

Further, the alkyl group represented by $R^3$ may be linear or branched, and examples thereof include a methyl group, an ethyl group, a propyl group, an isopropyl group, an n-butyl group, a sec-butyl group, a tert-butyl group, and an isobutyl group.

The alkoxyalkyl group having 2 to 6 carbon atoms represented by $R^3$ may be any of a linear group, a branched group, and a cyclic group (which means that two alkyl chains are combined together with an oxygen atom to form an oxygen-containing heterocycle), and specific examples thereof include a methoxymethyl group, an ethoxymethyl group, a 2-methoxyethyl group, and a 2-ethoxyethyl group.

The number of carbon atoms of the alkanoyl group represented by $R^3$ is preferably from 2 to 6. The alkanoyl group may be linear or branched, and examples thereof include an acetyl group, a propionyl group, and a tert-butylcarbonyl group.

The number of carbon atoms of the alkoxycarbonyl group represented by $R^3$ is preferably from 2 to 6. The alkoxycarbonyl group may be linear or branched, and examples thereof include a methoxycarbonyl group, an ethoxycarbonyl group, a propoxycarbonyl group, and a tert-butoxycarbonyl group.

The number of carbon atoms of the alkoxycarbonylalkyl group represented by $R^3$ is preferably from 2 to 6. The alkoxycarbonylalkyl group may be linear or branched, and examples thereof include a tert-butoxycarbonylmethyl group.

The number of carbon atoms of the alkylsilyl group represented by $R^3$ is preferably from 2 to 6. Examples of the alkylsilyl group include a trimethylsilyl group and a tert-butyldimethylsilyl group.

Further, m in the formula (3) is preferably 1 or 2, more preferably 1. Note that when m is 2 or 3, m number of —$OR^3$'s may be the same or different.

Hydrophobic Group (4):

[Chem. 5]

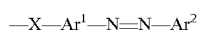

$$—X—Ar^1—N=N—Ar^2 \quad (4)$$

In the formula (4), X represents an ether linkage, a thioether linkage, a group —NH— or a group —OY— (wherein Y denotes an alkylene group and is linked to $Ar^1$ at one end thereof), $Ar^1$ represents a substituted or unsubstituted divalent aromatic hydrocarbon group, and $Ar^2$ represents a substituted or unsubstituted monovalent aromatic hydrocarbon group.

Examples of the alkylene group represented by Y include a methylene group, an ethylene group, a propylene group, a butylene group, a pentamethylene group, and a hexamethylene group.

Examples of the substituted or unsubstituted divalent aromatic hydrocarbon group represented by $Ar^1$ include a phenylene group, a naphthylene group, and an anthracylene group, and examples of the substituted or unsubstituted monovalent aromatic hydrocarbon group represented by $Ar^2$ include a phenyl group, a naphthyl group, and an anthracenyl group.

Further, as the hydrophobic group represented by the above formula (4), specifically, a 4-phenyldiazenylphenoxy group represented by the following formula (7) is exemplified.

[Chem. 8]

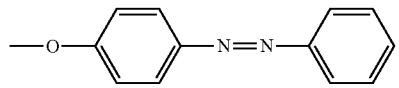

(7)

One or more hydrophobic groups (4) are included at a terminal of the hydrophobic group-containing polymer. The terminal may be any terminal of a main chain or a side chain, and may be any of both terminals and one terminal.

Further, the hydrophobic group-containing polymer used in the present invention may contain a structural unit (B) of the following formula (5) (hereinafter simply referred to as "structural unit (B)") having the above hydrophobic group (2).

[Chem. 6]

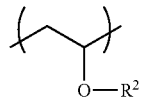

(5)

In the formula (5), $R^2$ has the same meaning as that in the above formula (2).

Further, the hydrophobic group-containing polymer used in the present invention may contain a structural unit (C) of the following formula (6) (hereinafter simply referred to as "structural unit (C)") having the above hydrophobic group (3).

[Chem. 7]

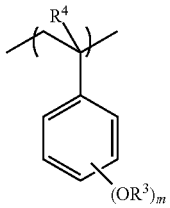

(6)

In the formula (6), $R^3$ and m have the same meanings as those in the above formula (3), and $R^4$ represents a hydrogen atom or an alkyl group having 1 to 4 carbon atoms, and the number of carbon atoms of the alkyl group is preferably 1 or 2.

Further, the alkyl group represented by $R^4$ may be linear or branched, and examples thereof include a methyl group, an ethyl group, a propyl group, an isopropyl group, an n-butyl group, a sec-butyl group, a tert-butyl group, and an isobutyl group.

When the hydrophobic group-containing polymer of the present invention contains the structural unit (B) or the structural unit (C), these may be used alone or combined. Further, the compositional ratio (molar ratio) of the structural unit (A), the structural unit (B), and/or the structural unit (C) can be arbitrary selected within a range not impairing a film forming property, water solubility, and a protein adsorption preventing property and is not particularly limited, but is preferably within a range of 99/1 to 10/90, more preferably within a range of 95/5 to 20/80, further more preferably within a range of 95/5 to 30/70, and particularly preferably within a range of 95/5 to 40/60.

In addition, when the hydrophobic group-containing polymer of the present invention further contains the structural unit (B) and/or the structural unit (C), the arrangement pattern of the structural unit (A) and the structural unit (B) and/or the structural unit (C) is not particularly limited, and the polymer may be either of a random copolymer and a block copolymer. Examples of the block copolymer include respective block polymers such as a diblock type (A-B, A-C, etc.), a triblock type (A-B-A, B-A-B, A-B-C, etc.), and a multi-branched star type ($[B-A]_n$, $[A-B]_n$, $[A-C]_n$, $A_nB_m$, etc., wherein n and m are the number of branches).

The molecular weight of the hydrophobic group-containing polymer of the present invention is, for example, from about 1,000 to 1,000,000, preferably from 2,000 to 500,000, more preferably from 3,000 to 300,000 as a weight average molecular weight (Mw) determined from a standard polystyrene calibration curve by gel permeation chromatography (GPC).

Further, the ratio (Mw/Mn) of the weight average molecular weight (Mw) to the number average molecular weight (Mn) of the hydrophobic group-containing polymer of the present invention is preferably from 1.0 to 5.0, more preferably from 1.0 to 3.0, and particularly preferably from 1.0 to 1.5. When Mw and Mw/Mn are within these ranges, the obtained hydrophobic group-containing polymer exhibits an excellent coating performance and an excellent protein adsorption preventing property.

In addition, specific examples of the hydrophobic group-containing polymer of the present invention include a copolymer containing the structural unit (A) and the structural unit (B) and/or the structural unit (C) (hereinafter simply referred to as "copolymer", a terminal-modified copolymer having the hydrophobic group (4) at a terminal of the copolymer (hereinafter simply referred to as "terminal-modified copolymer"), and a terminal-modified homopolymer having the hydrophobic group (4) at a terminal of a homopolymer containing the structural unit (A) (hereinafter simply referred to as "terminal-modified homopolymer"). Hereinafter, methods for producing these will be described.

(Copolymer)

The copolymer can be prepared by polymerizing a monomer giving the structural unit (A), a monomer giving the structural unit (B) and/or a monomer giving the structural unit (C) according to a conventional method. As a polymerization method at that time, particularly, a living cationic polymerization method is preferred for obtaining a copolymer having a desired compositional ratio and a desired molecular weight with good reproducibility. In the living cationic polymerization method, the molecular weight of the copolymer is almost uniquely determined by the molar ratio of the monomers and the polymerization initiator, and therefore, the molecular weight of the copolymer can be arbitrarily controlled in a wide range by changing the used amounts of the monomers and the polymerization initiator.

As the monomer giving the structural unit (A), a hydrophilic vinyl ether represented by the following formula (8) is exemplified. $R^1$ and n have the same meanings as those in the formula (1).

[Chem. 9]

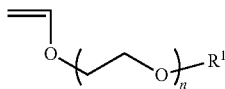

(8)

Specific examples of the hydrophilic vinyl ether (8) include 2-methoxyethyl vinyl ether (hereinafter referred to as "MOVE"), 2-ethoxyethyl vinyl ether (hereinafter referred to as "EOVE"), 2-(2-methoxyethoxy)ethyl vinyl ether (another name: diethylene glycol monomethyl monovinyl ether), 2-(2-ethoxyethoxy)ethyl vinyl ether (another name: diethylene glycol monoethyl monovinyl ether, hereinafter referred to as "EOEOVE"), 2-[2-(2-methoxyethoxy)ethoxy]ethyl vinyl ether (another name: triethylene glycol monomethyl monovinyl ether, hereinafter referred to as "TEGVE"), and 2-[2-(2-ethoxyethoxy)ethoxy]ethyl vinyl ether (another name: triethylene glycol monoethyl monovinyl ether). Among these, MOVE, EOVE, EOEOVE, TEGVE are preferred because they have an excellent film forming property and an excellent protein adsorption preventing property.

Further, as the monomer giving the structural unit (B), a hydrophobic vinyl ether represented by the following formula (9) is exemplified. $R^2$ has the same meaning as that in the formula (5).

[Chem. 10]

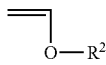

(9)

Specific examples of the hydrophobic vinyl ether (9) include n-butyl vinyl ether, isobutyl vinyl ether, cyclohexyl vinyl ether, and tricyclodecanyl vinyl ether. Among these, n-butyl vinyl ether and cyclohexyl vinyl ether are preferred.

Further, as the monomer giving the structural unit (C), a hydrophobic styrenic monomer represented by the following formula (10) is exemplified. $R^3$, $R^4$, and m have the same meanings as those in the formula (6).

[Chem. 11]

(10)

Specific examples of the hydrophobic styrenic monomer (10) include styrene; alkylstyrenes such as methylstyrene and ethylstyrene; hydroxystyrenes such as p-hydroxystyrene, m-hydroxystyrene, o-hydroxystyrene, p-isopropenylphenol, m-isopropenylphenol, and o-isopropenylphenol; alkoxystyrenes such as p-methoxystyrene, m-methoxystyrene, p-ethoxystyrene, m-ethoxystyrene, p-propoxystyrene, m-propoxystyrene, p-isopropoxystyrene, m-isopropoxystyrene, p-n-butoxystyrene, m-n-butoxystyrene, p-isobutoxystyrene, m-isobutoxystyrene, p-tert-butoxystyrene, and m-tert-butoxystyrene; alkoxyalkyloxy styrenes such as p-methoxymethoxystyrene, m-methoxymethoxystyrene, p-(1-ethoxyethoxy)styrene, m-(1-ethoxyethoxy)styrene, p-(2-tetrahydropyranyl)oxystyrene, and m-(2-tetrahydropyranyl)oxystyrene; alkanoyloxystyrenes such as p-acetoxystyrene, m-acetoxystyrene, p-tert-butylcarbonyloxystyrene, and m-tert-butylcarbonyloxystyrene; alkoxycarbonylalkyloxystyrenes such as p-tert-butoxycarbonylmethyloxystyrene and m-tert-butoxycarbonyloxymethylstyrene; and alkylsilyloxystyrenes such as p-trimethylsilyloxystyrene, m-trimethylsilyloxystyrene, p-tert-butyldimethylsilyloxystyrene, and m-tert-butyldimethylsilyloxystyrene, and among such oxystyrenic monomers, one type or two or more types may be used. Among these, hydroxystyrenes and alkoxystyrenes are preferred, and p-hydroxystyrene, p-isopropenylphenol, and p-tert-butoxystyrene are particularly preferred.

Further, the polymerization initiator to be used in the living cationic polymerization is not particularly limited as long as it allows cationic polymerization to proceed in a living manner, however, for example, as a living cationic polymerization initiator for a vinyl ether, an $HI/I_2$ initiator (for example, JP-A-60-228509), a polymerization initiator obtained by combining a Lewis acid catalyst (an organoaluminum compound, or the like) with an additive such as a base (an ether, an ester, or the like) (for example, Japanese Patent No. 3096494, JP-B-7-2805, JP-A-62-257910, JP-A-1-108202, and JP-A-1-108203), and the like are preferably used.

The used amount of the polymerization initiator is preferably from 0.001 to 20 mol %, more preferably from 0.01 to 10 mol %, and particularly preferably 1 mol % or less with respect to the total amount of the raw material monomers.

Further, the living cationic polymerization reaction is preferably performed in the presence of an appropriate organic solvent, but may be performed in the absence thereof. Examples of the organic solvent that can be used include aromatic hydrocarbon solvents such as benzene, toluene, and xylene; aliphatic hydrocarbon solvents such as propane, n-butane, isobutane, n-pentane, isopentane, n-hexane, n-heptane, n-octane, isooctane, decane, hexadecane, and cyclohexane; halogenated hydrocarbon solvents such as methylene chloride, ethylene chloride, and carbon tetrachloride; and ether solvents such as diethyl ether, dibutyl ether, tetrahydrofuran (THF), dioxane, and ethylene glycol diethyl ether. These organic solvents may be used alone or by combining two or more types as needed. Further, among these organic solvents, hydrocarbon solvents such as aromatic hydrocarbon solvents and aliphatic hydrocarbon solvents are preferred, and particularly, toluene or cyclohexane is preferred.

The polymerization temperature in the polymerization reaction varies depending on the type of the polymerization initiator, the monomer, or the solvent to be used, or the like, but is usually from −80 to 150° C., preferably from −50 to 100° C., and particularly preferably from −20 to 80° C. The polymerization time varies depending on the polymerization initiator, the monomer, or the solvent to be used, the reaction temperature, or the like, but is usually from about 10 minutes to 100 hours. The polymerization reaction can be favorably performed by either a batchwise method or a continuous method. After the polymerization reaction, if necessary, a purification treatment may be performed by a known method for removing unreacted monomers.

(Terminal-Modified Copolymer)

The terminal-modified copolymer can be produced by introducing the hydrophobic group represented by the above formula (4) at a terminal of the copolymer. A method for introducing the hydrophobic group (4) is not particularly limited, but for example, it can be performed by adding a compound capable of inducing the hydrophobic group (4) such as 4-phenylazophenol during the production of the copolymer and introducing a terminal structure at a terminal of a living polymer.

(Terminal-Modified Homopolymer)

The terminal-modified homopolymer can be produced by polymerizing the monomer giving the structural unit (A) according to a conventional method, and introducing the hydrophobic group (4) at a terminal of the obtained homopolymer, Note that the polymerization method can be performed in the same manner as the method for producing the copolymer described above, and the method for modifying the terminal can be performed in the same manner as the method for producing the terminal-modified copolymer described above.

On the other hand, in the protein adsorption preventing agent of the present invention, as for the aqueous solvent to be combined with the hydrophobic group-containing polymer, the type or the concentration thereof can be appropriately selected according to the composition or the molecular weight of the hydrophobic group-containing polymer, the type or the surface property of the substrate to become a coating target, or the like.

Examples of the aqueous solvent in the protein adsorption preventing agent of the present invention include water, an alcohol, and a ketone. As the alcohol, methanol, ethanol, isopropanol, and the like are preferred, and as the ketone, acetone, methyl ethyl ketone, and the like are preferred. Among these, water, isopropanol, ethanol and a mixed solvent thereof are preferred. These aqueous solvents may be used alone or by combining two or more types as needed.

In addition, the blending ratio of the hydrophobic group-containing polymer to the aqueous solvent in the protein adsorption preventing agent of the present invention is not particularly limited, however, with respect to 0.05 to 99 parts by mass of the hydrophobic group-containing polymer, 1 to 99.95 parts by mass of the aqueous solvent is preferred.

The preparation of the protein adsorption preventing agent of the present invention can be performed by a known method, but as a preferred preparation method, a method in which the hydrophobic group-containing polymer is blended in the aqueous solvent and uniformly stirred and mixed is exemplified.

The thus obtained protein adsorption preventing agent of the present invention is low toxic, has an excellent film forming property, and also is capable of forming a coating film having a protein adsorption preventing property. Therefore, the protein adsorption preventing agent of the present invention is used for forming a protein adsorption preventing film on various substrates, particularly a substrate that may come into contact with a protein component. Incidentally, the film forming property means that the protein adsorption preventing film is not peeled off from a substrate, and also the protein adsorption preventing film is not decomposed.

A method for forming the protein adsorption preventing film using the protein adsorption preventing agent of the present invention is not particularly limited, and is, for example, suitably selected from known methods such as a coating method, a spraying method, a dipping method, and a spin coating method according to a material, a shape, and a form of a substrate on which the protein adsorption preventing film is formed. For example, by a simple operation in which a substrate is immersed in the protein adsorption preventing agent, followed by drying or the like, the protein adsorption prevent film can be formed on the substrate. A time to immerse the substrate is not particularly limited, but is preferably from 0.5 to 24 hours. Further, as a drying method, air drying, heating drying, or the like is exemplified, and a drying time is not particularly limited, but is preferably from 0.5 to 5 hours. Further, a drying temperature is preferably from 25 to 80° C., more preferably from 25 to 50° C. Incidentally, the obtained protein adsorption preventing film can be directly applied to the below-mentioned medical tool together with the substrate, and further, the protein adsorption preventing film can also be used by being peeled off and adhered to another substrate.

The material, the shape, and the form of the substrate on which the protein adsorption preventing film is formed are not particularly limited, however, for example, an arbitrary shape or form such as a film, a sheet, a plate, a fiber, a non-woven fabric, a porous body, a tube, a hollow fiber, a particle, or a powder can be exemplified.

In addition, examples of the material of the substrate include synthetic resins and blend polymers thereof such as polyolefins such as polypropylene and polyethylene, nylon, polyester, polyacrylonitrile, a halogenated polyolefin, polystyrene, polycarbonate, polyvinyl chloride, polyurethane, polyamide, polysulfone, polyethersulfone, poly(meth)acrylate, an ethylene-vinylalcohol copolymer, a butadiene-acrylonitrile copolymer, and a cycloolefin polymer; natural polymers such as cotton and hemp; inorganic materials such as metals, ceramics, and glass, and composite materials thereof, and these can be used.

A medical tool can be exemplified as an example of a preferred thing in which the protein adsorption preventing film is formed using the protein adsorption preventing agent of the present invention. It is preferred that in the medical tool, at least a part, preferably the whole of a region coming into contact with a protein component is coated with the protein adsorption preventing film.

The medical tool of the present invention treated with the protein adsorption preventing agent in such a manner includes the protein adsorption preventing film, and therefore particularly can be preferably used in an application where it is used in direct contact with a protein. Specifically, it can be used in a wide range of fields of medical devices, sanitary products such as contact lenses, diagnostic agents, cell incubators, and the like.

EXAMPLES

The present invention will be more specifically described by way of the following Examples and Synthetic Examples, however, the present invention is by no means limited to these Examples and the like. Incidentally, in Examples, the compositional ratios of the polymers were determined from the results of analysis by $^1$H-NMR, and the weight average molecular weight (Mw) and the molecular weight distribution (Mw/Mn) were determined from the results of analysis of the molecular weight (in terms of polystyrene) by GPC. The analysis apparatuses and the measurement conditions, etc. are as follows.

(NMR)
 Apparatus: AVANCE 400 manufactured by Bruker
 Solvent: Deuterated acetone
 Measurement temperature: 30° C.
(GPC)
 Apparatus: "HLC-8320 GPC" manufactured by Tosoh Corporation
 Detector: RI detector
 Mobile phase: tetrahydrofuran
 Flow rate: 1 mL/min
 Column: "Shodex LF-804" manufactured by Showa Denko K.K.×3
 Column temperature: 40° C.

Synthesis Example 1

Synthesis of 2-(2-ethoxyethoxy)ethyl Vinyl Ether/Cyclohexyl Vinyl Ether Block Copolymer (EOEOVE-Block-CHVE)

In a 300-mL three neck flask equipped with a three-way stopcock which was dehydrated by heating at 300° C. or higher for 10 minutes under a dry nitrogen atmosphere, 170 mL of toluene as a solvent, 24.95 mL of ethyl acetate as an added base, 23.40 mL of diethylene glycol monoethyl monovinyl ether (EOEOVE) as a hydrophilic vinyl ether, and 0.25 mL of an acetic acid adduct of isobutyl vinyl ether as an initiating species were added and stirred well.

Then, the resulting mixture was maintained at −5° C., and 3.74 mL of $Et_{1.5}AlCl_{1.5}$ adjusted to 0.91 M was added thereto as a Lewis acid catalyst to initiate polymerization. At a stage when the conversion ratio of EOEOVE reached 95% or more, 4.82 mL of cyclohexyl vinyl ether was added thereto as a hydrophobic vinyl ether to perform polymerization.

The polymerization was terminated with methanol containing a small amount of sodium methoxide (1 M). An ion exchange resin [trade name: Amberlyst MSPS-2-DRY, manufactured by Organo Corporation] was added to the terminated solution to remove the Lewis acid. Subsequently, the resulting solution was passed through Celite, and further passed through a filter with a pore diameter of 1 μm, and then concentrated under reduced pressure with an evaporator, whereby a target block copolymer was obtained.

Synthesis Examples 2 to 6

Based on Synthesis Example 1, various polymers were prepared using EOEOVE, TEGVE, and MOVE as the hydrophilic vinyl ether, cyclohexyl vinyl ether (hereinafter referred to as "CHVE") and n-butyl vinyl ether (hereinafter referred to as "NBVE") as the hydrophobic vinyl ether, tert-butoxystyrene (hereinafter referred to as "TBOS") as a hydrophobic styrene monomer, respectively, by changing the amount of the initiating species, the Lewis acid species, the feeding order, and the terminator species.

The amount of the hydrophobic group (mol %), the molecular weight (Mw), the molecular weight distribution (Mw/Mn) and the solubility in water of each of the copolymers obtained in Synthesis Examples 1 to 6 are shown in Table 1.

TABLE 1

| Synthesis Example | Sample Name | Amount of hydrophobic group (mol %) | Mw | Mw/Mn | Solubility in water (25° C.) |
|---|---|---|---|---|---|
| 1 | EOEOVE-block-CHVE | 20 | 20,000 | 1.16 | Soluble |
| 2 | EOEOVE-ran-NBVE | | 20,500 | 1.15 | Soluble |
| 3 | EOEOVE-block-NBVE | | 20,500 | 1.13 | Soluble |
| 4 | TEGVE-block-NBVE | | 19,000 | 1.15 | Soluble |
| 5 | MOVE-block-NBVE | | 16,000 | 1.19 | Soluble |
| 6 | EOEOVE-block-TBOS | 5 | 19,000 | 1.23 | Soluble |

Synthesis Example 7

Synthesis of 4-(phenyldiazenyl)phenoxy Group-Containing EOEOVE

In a 300-mL three neck flask equipped with a three-way stopcock which was dehydrated by heating at 300° C. or higher for 10 minutes under a dry nitrogen atmosphere, 170 mL of toluene as a solvent, 24.95 mL of ethyl acetate as an added base, 23.40 mL of diethylene glycol monoethyl monovinyl ether (EOEOVE) as a hydrophilic vinyl ether, and 0.25 mL of an acetic acid adduct of isobutyl vinyl ether as an initiating species were added and stirred well. Then, the resulting mixture was maintained at −5° C., and 3.74 mL of $Et_{1.5}AlCl_{1.5}$ adjusted to 0.91 M was added thereto as a Lewis acid catalyst to initiate polymerization. At a stage when the conversion ratio of EOEOVE reached 95% or more, 4-phenylazophenol (manufactured by Sigma Aldrich Co.) was added in an amount of 1 g that is 3 times the amount of the initiating species to introduce 4-phenylazophenol at a terminal. To the resulting solution, an ion exchange resin [trade name: Amberlyst MSPS-2•DRY, manufactured by Organo Corporation] was added to remove the Lewis acid. Subsequently, the resulting solution was passed through Celite, and further passed through a filter with a pore diameter of 1 μm, and then concentrated under reduced pressure with an evaporator, whereby a terminal-modified homopolymer in which the terminal of EOEOVE was modified with a 4-(phenyldiazenyl)phenoxy group was obtained.

Synthesis Example 8

Synthesis of Methoxy Group-Containing EOEOVE

In a 300-mL three neck flask equipped with a three-way stopcock which was dehydrated by heating at 300° C. or higher for 10 minutes under a dry nitrogen atmosphere, 170 mL of toluene as a solvent, 24.95 mL of ethyl acetate as an added base, 23.40 mL of diethylene glycol monoethyl monovinyl ether (EOEOVE) as a hydrophilic vinyl ether, and 0.25 mL of an acetic acid adduct of isobutyl vinyl ether as an initiating species were added and stirred well. Then, the resulting mixture was maintained at −5° C., and 3.74 mL of $Et_{1.5}AlCl_{1.5}$ adjusted to 0.91 M was added thereto as a Lewis acid catalyst to initiate polymerization. At a stage when the conversion ratio of EOEOVE reached 95% or more, 1 M sodium methoxide was added thereto until the pH in the system reached near neutral pH to introduce methoxide at a terminal. To the resulting solution, an ion exchange resin [trade name: Amberlyst MSPS-2•DRY, manufactured by Organo Corporation] was added to remove the Lewis acid. Subsequently, the resulting solution was passed through Celite, and further passed through a filter with a pore diameter of 1 μm, and then concentrated under reduced pressure with an evaporator, whereby a terminal-modified homopolymer in which the terminal of EOEOVE was modified with a methoxy group was obtained.

The molecular weight (Mw), the molecular weight distribution (Mw/Mn), and the solubility in water of each of the polymers obtained in Synthesis Examples 7 and 8 are shown in Table 2.

TABLE 2

| Synthesis Example | Sample Name | Mw | Mw/Mn | Solubility in water (25° C.) |
|---|---|---|---|---|
| 7 | EOEOVE (containing 4-(phenyldiazenyl)phenoxy group at terminal) | 27,000 | 1.75 | Soluble |
| 8 | EOEOVE (containing methoxy group at terminal) | 22,000 | 1.16 | Soluble |

Examples 1 to 7

Protein Adsorption Preventing Agent:

A 5 mass % aqueous solution of each of the polymers obtained in the above Synthesis Examples 1 to 7 was prepared, whereby protein adsorption preventing agents (Examples 1 to 7) were obtained. In addition, a 5 mass % aqueous solution of Synthesis Example 8 was prepared as Comparative Example 1. Note that the protein adsorption preventing agents were all colorless and transparent.

Test Example 1

Protein Adsorption Preventing Property Test:

With respect to the protein adsorption preventing agents obtained in Examples 1 to 7 and the protein adsorption preventing agent obtained in Comparative Example 1, a protein adsorption preventing property test was performed by the following method. The results are shown in Table 3 below.

(1) Preparation of Polymer-Coated Well Plate 4 mL of each of the protein adsorption preventing agents of Examples 1 to 7 and Comparative Example 1 was added to a polystyrene 12-well plate, and left at room temperature for 16 hours. The protein adsorption preventing agent was removed from the well plate and then thoroughly washed with pure water. After washing, the well plate was dried in a dryer at 45° C. for 6 hours, whereby a well plate coated with each of the polymers of Synthesis Examples 1 to 8 was obtained.

(2) Preparation of Coloring Solution and Protein Solution

As a coloring solution, a mixture obtained by mixing bicinchoninic acid (hereinafter referred to as BCA solution) and a copper(II) sulfate solution at 50:1 was used.

As a protein solution, a solution obtained by adjusting a protein (Bovine Serum Albumin (IgG-Free Protease-Free), Immuno Research LABORATORIES, Inc.) to 30 μg/mL with a 0.1 M phosphate buffer solution (manufactured by Wako Pure Chemical Industries, Ltd.) was used.

(3) Protein Adsorption

The protein solution was dispensed (3 mL/well) to the 12-well plate in which the coating layer was formed from each of the polymers of Synthesis Examples 1 to 8 and left at room temperature for 3 hours.

(4) Well Washing

Subsequently, the 12-well plate was washed 4 times with 3 mL of the 0.1 M phosphate buffer solution.

(5) Dispensing of Coloring Solution

Subsequently, 2 mL of the coloring solution and 2 mL of the 0.1 M phosphate buffer solution were dispensed to the 12-well plate after washing, and a coloring reaction was performed at 65° C. for 1 hour.

(6) Preparation for Absorbance Measurement

Subsequently, 3 mL of the solution after completion of the coloring reaction was taken out into a PMMA cell and used as a sample for absorbance measurement.

(7) Absorbance Measurement

With respect to the absorbance, an absorbance at 562 nm was measured using a V-650 spectrophotometer manufactured by JASCO Corporation. The absorbance was converted to a protein adhesion amount from calibration curve data prepared in advance.

TABLE 3

| Example | Synthesis Example | Sample Name | Protein adhesion amount (μg/ml) |
|---|---|---|---|
| Example 1 | 1 | EOEOVE-block-CHVE | 0.05 |
| Example 2 | 2 | EOEOVE-ran-NBVE | 0 |
| Example 3 | 3 | EOEOVE-block-NBVE | 0 |
| Example 4 | 4 | TEGMVE-block-NBVE | 0 |
| Example 5 | 5 | MOVE-block-NBVE | 0 |
| Example 6 | 6 | EOEOVE-block-TBOS | 0.25 |
| Example 7 | 7 | EOEOVE (containing 4-(phenyldiazenyl)phenoxy group at terminal) | 0.26 |
| Comparative Example 1 | 8 | EOEOVE (containing methoxy group at terminal) | 0.42 |
| Comparative Example 2 | | Substrate uncoated with polymer (blank) | 0.42 |

It was confirmed that in the well plate in which the surface was coated with each of the protein adsorption preventing agents of Examples 1 to 7, the protein adsorption amount is smaller as compared with Comparative Example 1 and Comparative Example 2 (control).

INDUSTRIAL APPLICABILITY

As described above, a coating film formed from the protein adsorption preventing agent of the present invention has an excellent film forming property and excellent water solubility, and is capable of preventing protein adhesion. In particular, by forming such a coating film on a medical tool coming into contact with proteins, fouling can be prevented. Therefore, the present invention is extremely useful in the medical field and in the field of production of medical tools.

The invention claimed is:

1. A protein adsorption preventing agent, comprising:
a solvent, and
a water soluble polymer comprising
a structural unit (A) represented by the following formula (1):

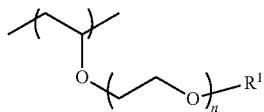

wherein
$R^1$ represents a methyl group or an ethyl group, and
n represents an integer of 1 to 10, and
a structural unit (B) of the following formula (5):

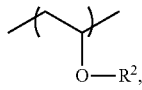

wherein in the formula (5), $R^2$ represents a linear or branched alkyl group or alkenyl group having 2 to 6 carbon atoms,
wherein the water soluble polymer is a random copolymer or block copolymer of the structural unit (A) and the structural unit (B), and
wherein the solvent is at least one selected form the group consisting of water, an alcohol, and a ketone.

2. The protein adsorption preventing agent according to claim 1, wherein a compositional ratio of the structural unit (A) and the structural unit (B) is from 99/1 to 10/90 in molar ratio.

3. The protein adsorption preventing agent according to claim 1, wherein an amount of the polymer is from 0.05 to 99 parts by mass, and an amount of the solvent is from 1 to 99.95 parts by mass, in the protein adsorption preventing agent.

4. A protein adsorption preventing film formed from the protein adsorption preventing agent according to claim 1.

5. A medical tool, comprising the protein adsorption preventing film according to claim 4.

6. A method for producing a protein adsorption preventing film, the method comprising immersing a substrate in the protein adsorption preventing agent according to claim 1, followed by drying.

7. The protein adsorption preventing agent according to claim 1, wherein n in the formula (1) is an integer of 3 to 10.

* * * * *